US012773535B2

(12) United States Patent
Amin

(10) Patent No.: US 12,773,535 B2
(45) Date of Patent: Oct. 27, 2026

(54) INTRAVENOUS ACCESS DEVICE FOR ADMINISTERING INTRAVENOUS FLUID

(71) Applicant: Nachiket Raghuvir Amin, Surat (IN)

(72) Inventor: Nachiket Raghuvir Amin, Surat (IN)

( * ) Notice: Subject to any disclaimer, the term of this patent is extended or adjusted under 35 U.S.C. 154(b) by 308 days.

(21) Appl. No.: 18/836,876

(22) PCT Filed: Oct. 30, 2023

(86) PCT No.: PCT/IN2023/050995
§ 371 (c)(1),
(2) Date: Aug. 8, 2024

(87) PCT Pub. No.: WO2024/079762
PCT Pub. Date: Apr. 18, 2024

(65) Prior Publication Data

US 2025/0082907 A1 Mar. 13, 2025

(30) Foreign Application Priority Data

Sep. 13, 2023 (IN) ............................ 202321061663

(51) Int. Cl.
*A61M 25/06* (2006.01)
*A61M 5/32* (2006.01)
*A61M 5/158* (2006.01)

(52) U.S. Cl.
CPC ........ *A61M 25/0618* (2013.01); *A61M 5/321* (2013.01); *A61M 2005/1587* (2013.01)

(58) Field of Classification Search
None
See application file for complete search history.

(56) References Cited

U.S. PATENT DOCUMENTS 9,474,880 B2 10/2016 Woehr et al.
2020/0297969 A1 9/2020 Abitabilo et al.

FOREIGN PATENT DOCUMENTS

AU 2009238275 12/2009
CN 101112639 1/2008
CN 113521494 B 5/2023
(Continued)

OTHER PUBLICATIONS

WIPO, International Search Report and Written Opinion for PCT/IN2023/050995, Jan. 30, 2024.
(Continued)

*Primary Examiner* — Manuel A Mendez
(74) *Attorney, Agent, or Firm* — HODGSON RUSS LLP

(57) ABSTRACT

The present disclosure relates to an intravenous access device (100) for administering intravenous fluids is disclosed, comprising a tube (102) having a proximal end (102*a*) and a distal end (102*b*) The distal end (102*b*) includes a beveled tip and is inserted into veins to access veins for administering intravenous fluids. A hub (104) is attached to the proximal end (102*a*) of the tube (102) and provides gripping support for the device (100). A needle (106) inside the tube (102) extends through the proximal end (102*a*) and the distal end (102*b*) of the tube (102). A clip (108) encapsulates a tip of the needle (106) during removal of the needle (106) and has a base (200) having a first set of fins, a plurality of crosspieces (204*a*, 204*b*) connected to the first set of fins (202*a*, 202*b*). The crosspieces (204*a*, 204*b*) are operably connected to each other and are arranged in an X-cross section position. A cage (110) is configured to encapsulate the clip (108) during removal of the needle (106).

15 Claims, 8 Drawing Sheets

(56) References Cited

FOREIGN PATENT DOCUMENTS

| | | | |
|---|---|---|---|
| ES | 2715456 | T3 | 6/2019 |
| WO | 2014138413 | | 9/2014 |

OTHER PUBLICATIONS

IPI, Office Action for IN Application No. 202321061663, Jun. 6, 2024.
WIPO, International Preliminary Report on Patentability for PCT/IN2023/050995, Oct. 16, 2025.
EPO, Extended European Search Report for EP Application No. 23876931.9, Feb. 2, 2026.

INTRAVENOUS ACCESS DEVICE FOR ADMINISTERING INTRAVENOUS FLUID

TECHNICAL FIELD

This disclosure generally relates to medical devices for transacting fluids in a body of a patient, not by way of limitation, to an intravenous access device for administering intravenous fluid.

BACKGROUND

Intravenous (IV) catheters play a critical role in modern healthcare by enabling healthcare professionals to administer fluids, medications, and other treatments directly into a patient's bloodstream. However, the insertion and management of IV catheters present certain challenges, particularly in terms of preventing accidental needlestick injuries and ensuring patient and healthcare worker safety. Traditional IV catheters lack adequate safety mechanisms to prevent unintentional needlestick injuries, which can lead to the transmission of bloodborne pathogens and other infections.

Incidentally, on an average, the workers suffer from approximately 30 needle stick injuries per 100 hospital beds per year. Most common cases of sharp injuries are unexpected patient reactions, shortage of staff, rushing, distraction, collision with another healthcare worker or passing equipment. These factors can't be controlled accidental needle stick injuries can happen to anyone. These injuries may cause of serious and potential fatal transmission of Hepatitis B or C viruses (HBV, HCV) or HIV. In fact nearly 90,000 healthcare workers worldwide contract Blood-borne injections annually (HBV, HCV, HIV).

Therefore, there is a need for an improved IV catheter with an innovative safety mechanism to address these concerns.

SUMMARY

In one embodiment, an intravenous access device for administering intravenous fluids is disclosed. The intravenous access device comprises a tube having a proximal end and a distal end. The distal end includes a beveled tip and is inserted into veins to access veins for administering intravenous fluids. The intravenous access device further comprises a hub attached to the proximal end of the tube. The hub provides gripping support for the intravenous access device when fielded. The intravenous access device further comprises a needle inside the tube and extending through the proximal end and distal end of the tube. The intravenous access device further comprises a clip configured to encapsulate a tip of the needle during removal of the needle. The clip comprises a base having a first set of fins, a plurality of crosspieces connected to the first set of fins. The plurality of crosspieces are operably connected to each other and are arranged in an X-cross section position. Upon exertion of a passive force, the plurality of crosspieces are capable of encapsulating the tip of the needle during removal of the needle. The clip further comprises a second set of fins connected to the first set of fins via the plurality of crosspieces. The second sets of fins are arranged at a top of plurality of the crosspieces. The intravenous access device further comprises a cage configured to encapsulate the clip during removal of the needle. The cage comprises a first aperture, a second aperture formed in a direction opposite to a location of the first aperture and slightly lower to the location of the first aperture, and a plurality of slits formed at a bottom of the cage.

The design of the IV catheter takes patient comfort into consideration. The catheter features a tapered and polished tip that facilitates smooth insertion into the vein, reducing patient discomfort during the process. Additionally, the catheter hub is ergonomically designed, providing a comfortable grip for healthcare professionals during insertion and activation of the safety mechanism.

The IV catheter with safety mechanism is designed to be compatible with standard IV administration sets and equipment, ensuring seamless integration into existing healthcare workflows. Passive force activated safety mechanism is for easy access and intuitive use, enabling healthcare professionals to quickly adopt the new safety technology without extensive training.

The safety mechanism is engineered to function reliably and consistently, minimizing the risk of malfunctions that could compromise patient safety or healthcare worker effectiveness.

The IV catheter design allows for different sizes and configurations to accommodate various patient populations and clinical scenarios. This customization ensures that the safety mechanism remains effective across diverse healthcare contexts.

Further areas of applicability of the present disclosure will become apparent from the detailed description provided hereinafter. It should be understood that the detailed description and specific examples, while indicating various embodiments, are intended for purposes of illustration only and are not intended to necessarily limit the scope of the disclosure.

BRIEF DESCRIPTION OF THE DRAWINGS

The present disclosure is described in conjunction with the appended figures.

In the appended figures, similar components and/or features may have the same reference label. Further, various components of the same type may be distinguished by following the reference label by a second alphabetical label that distinguishes among the similar components. If only the first reference label is used in the specification, the description is applicable to any one of the similar components having the same first reference label irrespective of the second reference label.

DETAILED DESCRIPTION OF THE DRAWINGS

The ensuing description provides preferred exemplary embodiment(s) only, and is not intended to limit the scope, applicability or configuration of the disclosure. Rather, the ensuing description of the preferred exemplary embodiment (s) will provide those skilled in the art with an enabling description for implementing a preferred exemplary embodiment. It is understood that various changes may be made in the function and arrangement of elements without departing from the spirit and scope as set forth in the appended claims.

Embodiments described herein are generally related devices for administering intravenous fluid in the body of a patient. In particular, some embodiments of the disclosure describe processes for removing a needle from the body of the patient without causing pain, discomfort and injury to the patient and a medical operator performing a task of administering intravenous fluids from the body of the patient.

The disclosure specifically indicates that upon retracting of the needle, how a clip encapsulates a tip of the needle and further how clip is encapsulated by a cage of the intravenous access device. This eliminates the risk of accidental needlestick injuries to the patient or a medical operator during the removal of the needle.

Figure 1:
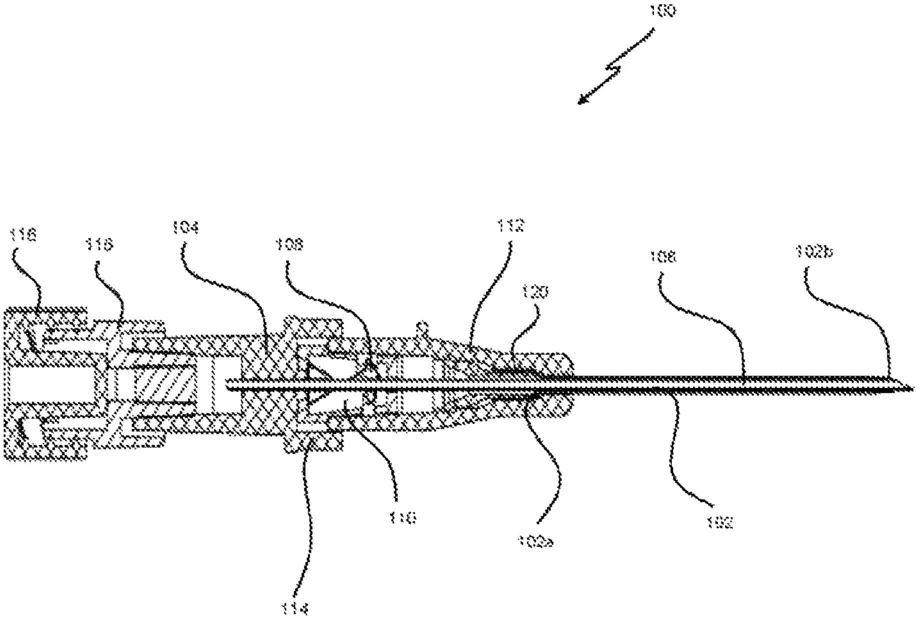
FIG. 1 illustrates a cross sectional view of an intravenous access device according to an embodiment of the present disclosure.

Referring to FIG. 1, it illustrates a cross sectional view of an intravenous access device 100 according to an embodiment of the present disclosure. The intravenous access device 100 comprises a tube 102, a hub 104, a needle 106, a clip 108, a cage 110, an external housing 112, a stabilizer 114, a sealing mechanism 116, a cover body 118, and a Teflon holder 120.

For administering intravenous fluids, a medical professional operates the intravenous access device 100, where the tube 102 has a proximal end 102*a* and a distal end 102*b*. In some embodiments, the intravenous access device 100 may refer to the intravenous (IV) catheter or IV cannula and may be used interchangeably for the clarity of the description of embodiments. The IV cannula is a sterile, non-toxic, and pyrogen-free medical device used to deliver nutritional fluids, saline, medications, or blood products to patient's vascular system. The IV cannula is intended for single-use. The IV cannula is intended to be used for all patients. The needle 106 of IV cannula, which is inserted in the body of the patient during venipuncture may have been exposed to infectious agents. For example, a patient infected with the Acquired Immune Deficiency Syndrome (AIDS) which is frequently or practically fatal in nature, or other dangerous infectious conditions such as Hepatitis B and C virus, there is a constant danger or hazard that the clinical personnel or the para-medical staff may accidentally stick themselves with the used needle after withdrawal from the body of the patient, with the possibility of infection or even death resulting therefrom.

The term "tube" typically refers to the flexible plastic tubing that may be connected to the hub 104 on one end and to a fluid source on the other end. The role of the tube 102 in an IV catheter is to serve as a conduit through which fluids can flow from the source (such as an IV bag or syringe) into the patient's bloodstream. The distal end 102*b* includes a beveled tip, and the distal end 102*b* is inserted into veins to access veins for administering the intravenous fluids. Overall, the tube 102 in an IV catheter plays a critical role in delivering fluids, medications, electrolytes, and other therapeutic substances directly into the patient's circulatory system. This method of administration is efficient and rapid, making it suitable for situations where timely and precise delivery of fluids or medications is required. In some embodiments, the tube 102 is made from at least one of a polyvinyl chloride (PVC), polyethylene (PE), polypropylene etc, however the choice of tubing material depends on factors such as the intended use of the tubing, the specific medical application, biocompatibility requirements, regulatory standards to ensure patient safety and device effectiveness, and the types of fluids or medications that will flow through the tube 102.

The hub 104 also known as catheter hub is attached to the proximal end 102*a* of the tube 102. The hub 104 provides gripping support for the intravenous access device 100, when fielded. The catheter hub 104 is the part of the IV catheter that contains parts inserted into the patient's vein. The catheter hub 104 may include a small plastic hub with a needle or catheter tube extending from it.

In some embodiments, the intravenous access device 100 includes a regulator or a flow control device on the tube 102 that may be adjusted to regulate the rate of fluid infusion. This allows healthcare providers to control the flow rate and ensure that fluids are administered at the appropriate speed. In some embodiments, an external housing 112 of the tube 102 is usually equipped with a mechanism to secure the tube in place, such as a winged grip or adhesive.

The needle 106 is arranged inside the tube 102, and extends through the proximal end 102*a* and the distal end 102*b* of the tube 102. The clip 108 is configured to encapsulate a tip of the needle 106 during removal of the needle 106. Additionally the cage 110 is configured to encapsulate the clip 108 during removal of the needle 106.

In some embodiments, the external housing 112 is configured to accommodate the tube 102. In some embodiments, the external housing is made from (PP) Polypropylene Random Copolymer K-RESIN (clear styrene-butadiene block copolymer). The stabilizer 114 is connected to the hub 104 for stabilizing the intravenous access device 100 during insertion and removal.

In some embodiments, the intravenous access device 100 further comprises a cover body configured to cover the hub 104 and a sealing mechanism configured to seal the cover body for intravenous fluids. To prevent fluid leakage from IV catheter tubes, various types of seals and connections are used to ensure a secure and leak-free connection between different components. These seals are crucial to maintaining the integrity of the IV system and preventing any contamination or fluid loss. In some examples, the sealing mechanism may be chosen from at least one of a threaded stopper, luer-lock connector, gasket seals, press-fit seals bayonet locks and adhesive seals.

In some embodiments, the intravenous access device 100 further comprises an indicator to visually indicate proper encapsulation of the clip 108 and the needle 106 inside the cage 110. For example, the indicator may be a transparent window through which healthcare providers can visually confirm that the needle is retracted and locked. This can provide a clear view of the needle's status without the need for direct handling. In another example, a portion of indicator may change color once the needle 106 is safely retracted and locked, providing a visible confirmation. In another example, the indicator may be an audible indicator, such as a click or sound, can provide feedback when the needle is successfully retracted and locked. This auditory cue can be reassuring to healthcare providers. The indicators are designed to give healthcare providers clear and immediate feedback that the needle 106 has been safely retracted and locked after use. The exact design and implementation of the indicators may vary according to application attributes.

The intravenous access device 100 further comprises a release mechanism arranged inside the tube 102 to perform locking of the clip 108 to encapsulate the tip of the needle 106, and encapsulating of the clip 108 by the cage 110 during removal of the needle 106. In some embodiments, the release mechanism comprises two secure-elements, each of the secure elements configured to function on an unlocking angle to perform locking of the clip 108 to encapsulate the tip of the needle 106 upon exertion of a passive force. In an example, each one of the secure elements operate in the range of 287 degrees to 293 degrees. The Teflon holder 120 helps to the joint of the device 100 and the housing 112 and avoids leakage of the blood.

Figure 2:
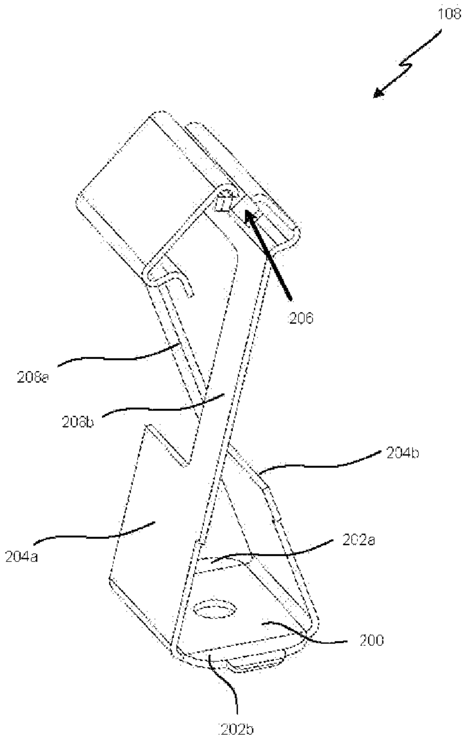
FIG. 2 illustrates a perspective view of a clip according to an embodiment of the present disclosure.

Referring to FIG. 2, it illustrates a perspective view of the clip 108 according to an embodiment of the present disclosure. The clip 108 is similar to the clip of in FIG. 1. The clip 108 is a safety mechanism that is designed to reduce the risk of needlestick injuries to patients and healthcare providers when retracting needles from a patient's body. Needlestick injuries can occur when a healthcare worker accidentally comes into contact with a used needle, potentially exposing themselves to bloodborne pathogens and infections. The clip 108 is specifically designed to minimize this risk by automatically retracting the needle into a protective housing after use.

The clip 108 has primary functions of needle retraction and locking needle tip. In some embodiments the clip 108 includes an activation system to ensure that the clip 108 is activated by a deliberate action taken by the healthcare provider, such as applying passive force. The clip 108 has structural components to perform needle retraction and locking.

The clip 108 comprises a base 200 having a first set of fins 202*a*, 202*b*. A plurality of crosspieces 204*a*, 204*b* is connected to the first set of fins 202*a*, 202*b*. The plurality of crosspieces 204*a*, 204*b* are operably connected to each other and are arranged in an X-cross position. Upon exertion of a passive force, the plurality of crosspieces 204*a*, 204*b* are capable of encapsulating the tip of the needle 106 during removal of the needle 106. The clip further comprises a second set 206 of fins connected to the first set of fins 202*a*, 202*b* via the plurality of crosspieces 204*a*, 204*b*. The second set of fins are arranged at a top of plurality of the crosspieces.

In some embodiments, the base 200 has the first set of fins that is operably connected to the crosspieces via a pivot-joint mechanism. The pivot-joint mechanism may refer to a type of mechanical linkage that enables two components to rotate around a common axis. It allows for relative motion between the two components while maintaining a fixed point of rotation. This type of mechanism is often used in various devices to achieve controlled rotation or angular movement. In such case, the first set of fins and the crosspieces may have a common mechanical linkage that enables the first set of fins and the crosspieces to rotate around a common axis.

In some embodiments, the plurality of crosspieces 204*a*, 204*b* comprises arms 208*a*, 208*b* to lock the tip of the needle during removal of the needle in the X-cross position. In lock position, the plurality of crosspieces 204*a*, 204*b* are secured by the arms 208*a*, 208*b*. In some embodiments, the clip 108 is made of steel. In some embodiments, the plurality of crosspieces comprises two arms having equal lengths. In some embodiments, the two arms are operably connected to each other via a spring-mechanism, and the spring mechanism is configured to maintain a default position of the arms. In some embodiments, the crosspieces comprise two arms having variable lengths.

Figure 3:
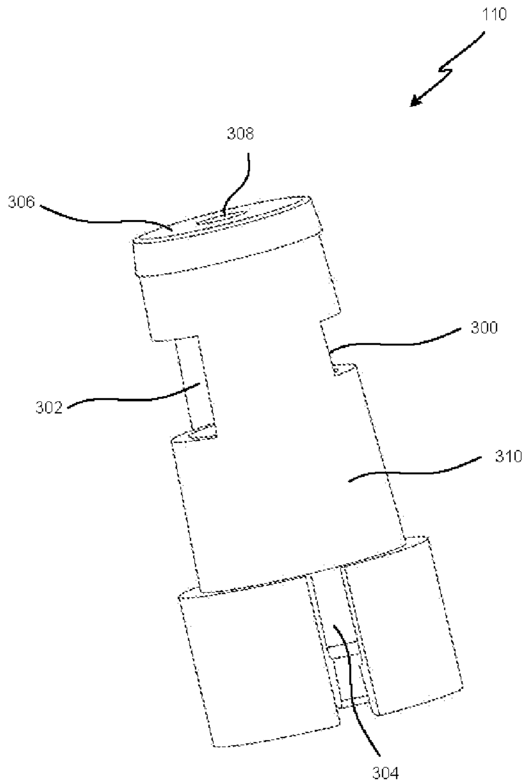
FIG. 3 illustrates a front perspective view of a cage according to an embodiment of the present disclosure.

Referring to FIG. 3, it illustrates a front perspective view of the cage 110 according to an embodiment of the present disclosure. The cage 110 is similar to the cage of in FIG. 1.

The cage 110 is configured to encapsulate the clip 108 during removal of the needle 106. The cage 110 refers to an additional protective mechanism that is used in conjunction with the clip 108 to enhance needlestick prevention and minimize the risk of accidental injuries. This cage 110 adds an extra layer of physical protection over the needle 106 and the clip 108, further reducing the potential for needlestick incidents. In other words, a combination of the clip 108 and the cage 110 provide a passive safety technology with double protection.

In some embodiments, the cage 110 is typically designed to fit securely over the clip 108, enclosing the needle 106 and clip 108 within a protective housing. In some embodiments, the cage 110 may use a hinging mechanism that allows the cage 110 to be easily opened and closed like a clamshell. In some other embodiments, the cage 110 may have a snap-on design that fits tightly over the clip 108.

In some embodiments, the cage 110 is made of durable materials, such as plastic, that provide a physical barrier to prevent accidental contact with the needle 106. In some embodiments, the cage 110 is made of materials selected from a group of polypropylene random copolymer, polypropylene homopolymer, high-density polyethylenek-resin (clear styrene-butadiene block copolymer), polycarbonate, polyoxymethylene, and acrylonitrile butadiene styrene.

In some embodiments, the cage 110 may have mechanisms to securely lock the needle 106 in place, ensuring that the needle 106 remains covered and protected until it is intentionally removed by the healthcare professional.

The cage 110 comprises a first aperture 300 and a second aperture 302. The second aperture 302 is formed in a direction opposite to a location of the first aperture 300 and slightly lower to the location of the first aperture 300. The cage further comprises and one or more slits 304 formed at a bottom of the cage 110. The one or more slits 304 affixes the cage 110 to the hub 104. In some embodiments, the first aperture 300 and the second aperture 302 may have a circular shape. In some other embodiments, the first aperture 300 and the second aperture 302 may have a square shape. In some embodiments, each of the first aperture 300 and the second aperture 302 may have an interchangeably square shape or circular shape. Specifically, in the embodiment of FIG. 3, the first aperture 300 and the second aperture 302 have a rectangular shape. In some embodiments, the first aperture 300 and the second aperture 302 have an area in the range from 0.5 (millimeters) mm to 1.30 mm. In some embodiments, the first aperture 300 and the second aperture 302 have an area in the range from 0.6 mm to 1.20 mm. In some embodiments, the first aperture 300 and the second aperture 302 have an area in the range from 0.7 mm to 1.10 mm. In some embodiments, the first aperture 300 and the second aperture 302 have an area in the range from 0.8 mm to 1 mm. In some embodiments, the first aperture 300 and the second aperture 302 have an area 0.9 mm. In some embodiments, an area of the first aperture 300 is greater than an area of the second aperture 302. In some other embodiments, an area of the first aperture 300 is lesser than an area of the second aperture 302.

In some embodiments, the cage 110 has a frustum-conical structure and comprises a top surface 306 having a hole 308. In some embodiments, the hole 308 has a diameter in a range from 0.1 mm to 0.5 mm. In some embodiments, the hole 308 has a diameter in a range from 0.2 mm to 0.4 mm. In some embodiments, the hole 308 has a diameter 0.3 mm. In other words, the dimensions of the first aperture 300, the second aperture 302, and the hole 308 are formed corresponding to the dimensions of structural components of clip 108, such that each of the structural components of clip 108 are complimented and are able to fit inside the cage 110 during both locking and unlocking position of the arms of the cage. In some embodiments, the cage 110 has a cylindrical structure.

The cage 110 further comprises a lateral surface 310. The first aperture 300 is formed at the lateral surface 310 and near to the top surface 306. In some embodiments, the first set of fins forms interlocking with the one or more slits and the second set of fins forms interlocking with the first aperture and the second aperture of cage 110 to stop rotational movement of the clip 108 and a lateral movement of cage 110.

FIG. 4A to FIG. 4D, illustrate schematic representations of a process of retracing a needle and locking the needle tip with clip and cage. The process indicates locking the movement of the needle and providing coverage and protection of the tip of the needle 106 by the clip 108 and further with the cage 110.

Figure 4A:
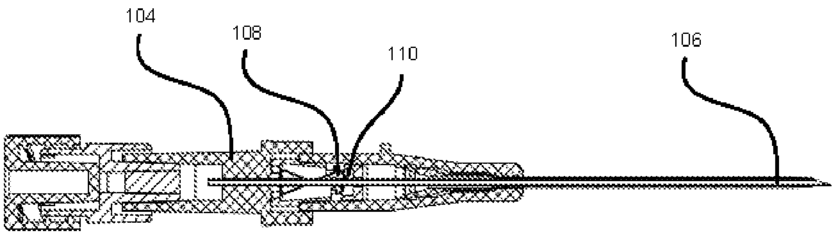
FIG. 4A to 4D illustrate schematic representations of a process of retracing a needle and locking the needle tip with clip and cage according to an embodiment of the present disclosure.

Referring to FIG. 4A, the intravenous access device 100 is in ready to use position, where needle 106 is exposed and ready to insert into veins to access veins for administering intravenous fluids. The clip 108, in its initial state, is positioned in the external housing 112 of tube 102 near the needle 106 but does not cover the needle tip. A cage 110 is also positioned in the external housing 112 of tube 102 above the clip 108.

Figure 4B:
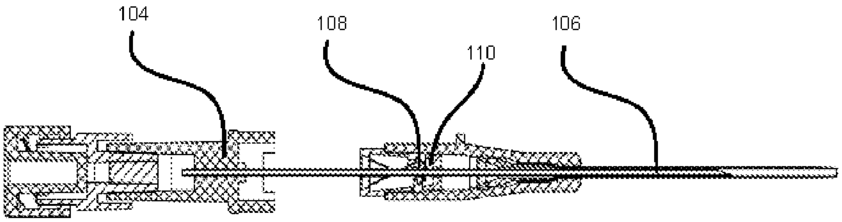

Referring to FIG. 4B, after the completion of insertion of needle into intravenous vein, the user needs to apply a certain level of passive force which enables the hub 104 to glide backward to start the retracting of needle.

Figure 4C:
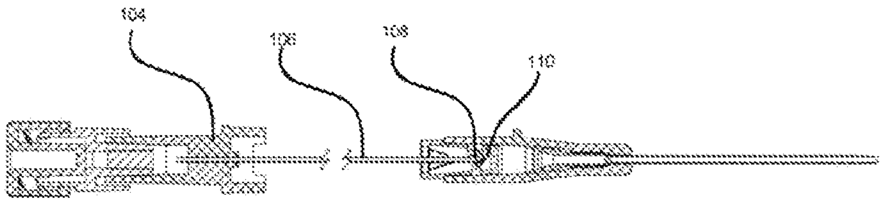

Referring to FIG. 4C, as the user further applies passive force, the hub 104 further glides backward and the needle tip is encapsulated by plurality X-cross pieces of clip 108. The sliding or pivoting mechanism is designed to move in a specific trajectory. As it moves, clip in a position that fully covers the needle tip in a controlled manner.

Figure 4D:
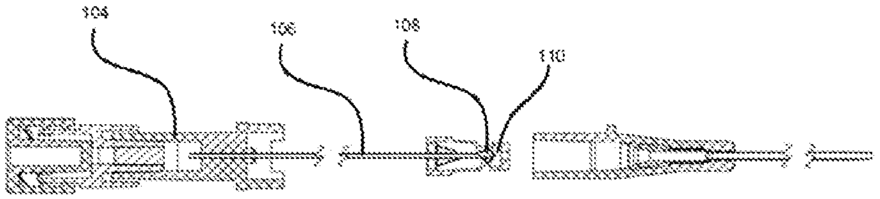

Referring to FIG. 4D, once the hub 104 completes the gliding, the needle 106 is now in retracting position and clip is fully covering the needle tip. At end of retraction, the dent near the needle tip pulls a cage 110 which encapsulates the clip 108. Further the first set of fins of the clip 108 form an interlocking with the one or more slits of the cage 110 while the second set of fins of the clip form an interlocking with the first aperture and the second aperture of the cage 110. These interlockings not only stop rotational movement of the clip but also stop lateral movement of cage.

This ensures that the needle is safely concealed within the double safety mechanism, significantly reducing the risk of accidental needlestick injuries.

To summarize the above, when the needle 106 is pulled backwards, the needle 106 comes in contact with the clip 108 to lock the tip of the needle in an X-Cross position to completely prevent further axial or rotational movement with respect to each other. This leads to fixing of a needle dent on a backside of the clip 108 and thus forward and backward direction of the needle 106 is interlocked. Further, when the needle 106 is withdrawn in a backward direction, the cage 110 gets activated, and the tip of the needle 106 is covered by the cage 110. At this position, the cage 110 and the clip 108 are in an irreversible locking position.

Figure 5A:
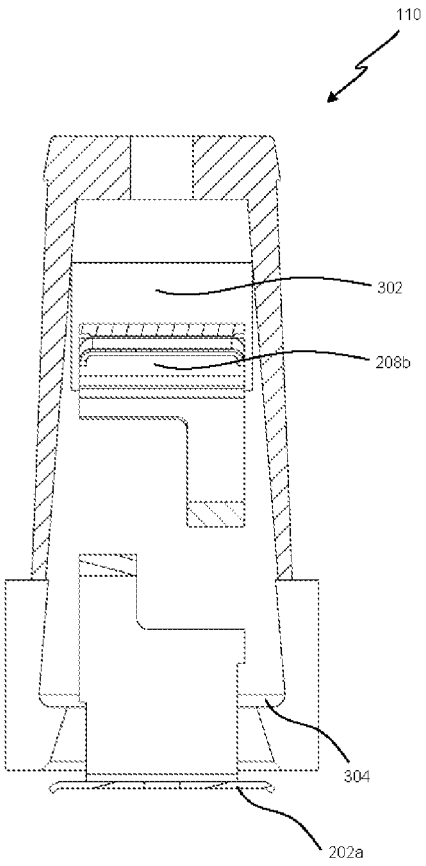
FIG. 5A to 5C illustrate schematic representations of a process of interlocking of the crosspieces arms, the first set of fins and the second set of fins of clip with the first aperture, the second aperture and the slits of cage according to an embodiment of the present disclosure.
Figure 5B:
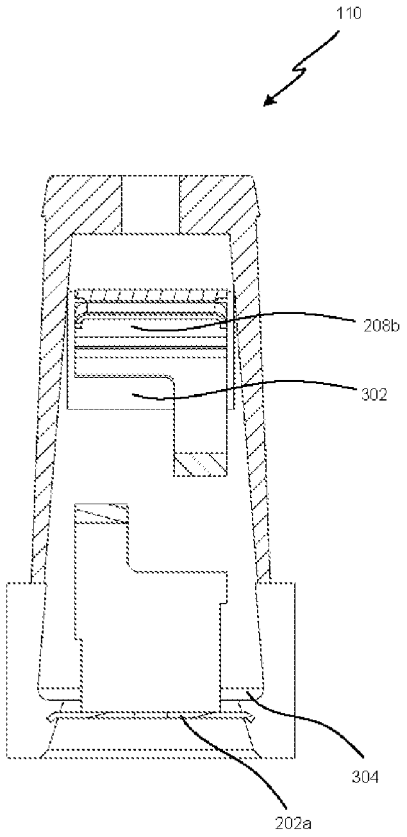
Figure 5C:
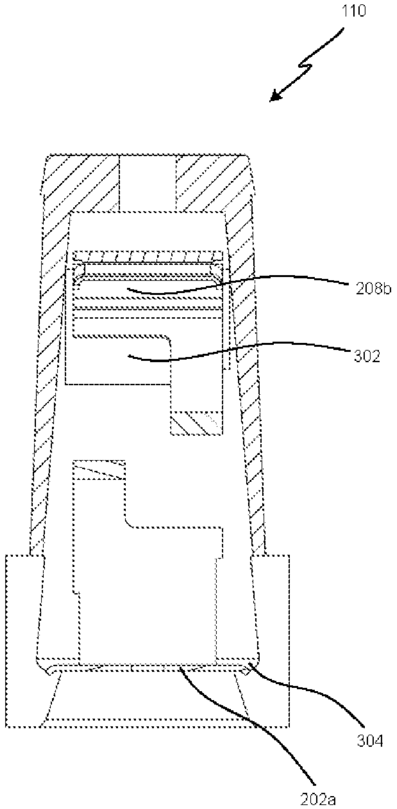

FIG. 5A to FIG. 5C, illustrate schematic representations of a process of interlocking of the crosspieces, the first set of fins and the second set of fins of clip 108 with the first aperture, the second aperture and the slits of cage 110 according to an embodiment of the present disclosure. As shown the crosspieces 208*a*, 208*b* of clip 108 form interlocking with the first aperture 300 and the second aperture 302 of cage 110 to stop a lateral movement of cage 110. Further the first set of fins 202*a*, 202*b* and the second set 206 of fins of the clip 108 form interlocking with the slits 304 of cage 110 to stop rotational movement of the clip 108.

Referring to FIG. 5A, at initial state, crosspieces and set of fins of the clip are disconnected with apertures and slits of the cage. As represented in FIG. 5A, one of the crosspieces 208*b* of the clip is in disconnected state with the second aperture 302 of cage 110. Similarly, one of the fins 202*a* of the clip is in disconnected state with the slit 304 of the cage 110. At this state, both crosspieces and set of fins of the clip is not locked with apertures and slits of the cage and hence the clip is free to move and rotate.

Referring to FIG. 5B, at partial interlocking state, crosspieces and set of fins of the clip are partially connected with apertures and slits of the cage. As represented in FIG. 5B, one of the crosspieces 208*b* of the clip is in partially interlocking state with the second aperture 302 of cage 110. Similarly, one of the fins 202*a* of the clip is in partially connected with the slit 304 of the cage 110. At this state, both crosspieces and set of fins of the clip are partially interlocked with apertures and slits of the cage and hence prevents the rotational movement of the clip 108.

Referring to FIG. 5C, at fully interlocking state, crosspieces and set of fins of the clip are completely connected with apertures and slits of the cage. As represented in FIG. 5C, one of the crosspieces 208*b* of the clip is in fully interlocking state with the second aperture 302 of cage 110. Similarly, one of the fins 202*a* of the clip is in fully interlocking state with the slit 304 of the cage 110. At this state, both crosspieces and set of fins of the clip are fully interlocked with apertures and slits of the cage and hence prevents both the rotational as well as the lateral movement of the clip 108.

The present disclosure relates to an innovative intravenous (IV) catheter with an integrated dual-safety mechanism designed to reduce the risk of needlestick injuries, enhance patient comfort, and streamline the catheter insertion process. The IV catheter with safety mechanism combines advanced engineering and user-centric design to provide a comprehensive solution for healthcare settings.

While particular embodiments have been described and illustrated, it should be understood that the scope of the disclosure is not limited to these specific examples. Variations and modifications within the scope of the appended claims will be readily apparent to those skilled in the art. Therefore, the present disclosure is not to be limited to the embodiments disclosed herein but is to be accorded the widest scope consistent with the principles and novel features disclosed herein.

Accordingly, the present disclosure should not be construed as limited by the foregoing description, but rather construed in accordance with the appended claims. Specific details are given in the above description to provide a thorough understanding of the embodiments. However, it is understood that the embodiments may be practiced without these specific details. Also, it is noted that the embodiments may be described as a process which is depicted as a schematic representation. Although a depiction may describe the operations as a sequential process, many of the operations can be performed in parallel or concurrently.

The systems and devices discussed herein are examples. Various configurations may omit, substitute, or add various procedures or components as appropriate. For instance, in alternative configurations, the methods may be performed in an order different from that described, and/or various stages may be added, omitted, and/or combined. Also, features described with respect to certain configurations may be combined in various other configurations. Different aspects and elements of the configurations may be combined in a similar manner. Also, technology evolves and, thus, many of the elements are examples and do not limit the scope of the disclosure or claims. Additionally, the techniques discussed herein may provide differing results with different types of context awareness classifiers.

Unless defined otherwise, all technical and scientific terms used herein have the same meaning as commonly or conventionally understood. As used herein, the articles "a" and "an" refer to one or to more than one (i.e., to at least one) of the grammatical object of the article. By way of example, "an element" means one element or more than one element. "About" and/or "approximately" as used herein when referring to a measurable value such as an amount, a temporal duration, and the like, encompasses variations of +20% or +10%, +5%, or +0.1% from the specified value, as such variations are appropriate to in the context of the systems, devices, circuits, methods, and other implementations described herein. "Substantially" as used herein when referring to a measurable value such as an amount, a temporal duration, a physical attribute (such as frequency), and the like, also encompasses variations of +20% or +10%, +5%, or +0.1% from the specified value, as such variations are appropriate to in the context of the systems, devices, circuits, methods, and other implementations described herein.

As used herein, including in the claims, "and" as used in a list of items prefaced by "at least one of" or "one or more of" indicates that any combination of the listed items may be used.

I claim:

1. An intravenous access device comprising:

a tube having a proximal end and a distal end, wherein:
 the distal end includes a beveled tip, and
 the distal end is inserted into veins to access veins for administering intravenous fluids;
a hub attached to the proximal end of the tube, wherein the hub provides gripping support for the intravenous access device, when fielded;
a needle inside the tube, and extending through the proximal end and the distal end of the tube;
a clip configured to encapsulate a tip of the needle during removal of the needle, the clip comprising:
 a base having:
  a first set of fins;
  a plurality of crosspieces connected to the first set of fins, wherein the plurality of crosspieces are operably connected to each other and are arranged in an X-cross position, and wherein upon exertion of a passive force, the plurality of crosspieces are capable of encapsulating the tip of the needle during removal of the needle, and
  a second set of fins connected to the first set of fins via the plurality of crosspieces, wherein the second set of fins are arranged at a top of plurality of the crosspieces;
a cage configured to fit securely over the clip, enclosing the clip and the needle within a protective housing during removal of the needle, the cage comprising:
 a first aperture,
 a second aperture formed in an opposite wall of the cage and positioned vertically below the first aperture by a distance corresponding to a vertical offset of the second set of fins, such that each fin in the second set of fins is received into a respective aperture when the clip is in a locked position, and
 one or more slits formed at a bottom of the cage,
wherein the first set of fins forms interlocking with the one or more slits and the second set of fins forms interlocking with the first aperture and the second aperture of the cage to stop rotational movement of the clip and a lateral movement of the cage.

2. The intravenous access device as claimed in claim 1, wherein the intravenous access device comprising:
an external housing configured to accommodate the tube;
a cover body configured to cover the hub; and
a sealing mechanism configured to seal the cover body for intravenous fluids.

3. The intravenous access device as claimed in claim 1, wherein the plurality of crosspieces comprises arms to lock the tip of the needle during removal of the needle in the X-cross position, wherein when in lock position, the plurality of crosspieces are secured by the arms.

4. The intravenous access device as claimed in claim 1, wherein the cage has a frustum-conical structure and comprises:
a top surface having a hole; and
a lateral surface,
wherein the one or more slits affixes the cage to the hub, and the first aperture is formed at the lateral surface and near to the top surface.

5. The intravenous access device as claimed in claim 4, wherein an area of the first aperture is greater than an area of the second aperture.

6. The intravenous access device as claimed in claim 4, wherein an area of the first aperture is lesser than an area of the second aperture.

7. The intravenous access device as claimed in claim 1, the intravenous access device comprising an indicator to visually indicate proper encapsulation of the clip and the needle inside the cage.

8. The intravenous access device as claimed in claim 1, the intravenous access device comprising a release mechanism arranged inside the tube, the release mechanism including a pair of secure-elements configured to be actuated by a passive force applied by the hub to:
lock the clip to encapsulate the tip of the needle, and
activate the cage to fit securely over the clip during removal of the needle.

9. The intravenous access device as claimed in claim 8, wherein the release mechanism comprises two secure-elements, each of the two secure elements configured to function on an unlocking angle to perform locking of the clip to encapsulate the tip of the needle upon exertion of the passive force.

10. The intravenous access device as claimed in claim 1, wherein the clip is made of steel.

11. The intravenous access device as claimed in claim 1, wherein the plurality of crosspieces comprises two arms having equal lengths.

12. The intravenous access device as claimed in claim 11, wherein, the two arms are operably connected to each other via a spring-mechanism, and wherein the spring mechanism is configured to maintain a default position of the arms.

13. The intravenous access device as claimed in claim 1, wherein the crosspieces comprise two arms having variable lengths.

14. The intravenous access device as claimed in claim 1, wherein the base having first set of fins is operably connected to the crosspieces via a pivot-joint mechanism.

15. The intravenous access device as claimed in claim 1, wherein the cage is made of materials selected from a group of polypropylene random copolymer, polypropylene homopolymer, high-density polyethylenek-resin (clear styrene-butadiene block copolymer), polycarbonate, polyoxymethylene, and acrylonitrile butadiene styrene.

* * * * *